(12) United States Patent
Propp et al.

(10) Patent No.: US 6,733,508 B1
(45) Date of Patent: May 11, 2004

(54) UMBILICAL CORD CLAMP CUTTER

(75) Inventors: Donald J. Propp, Dewitt, MI (US); Gary A. Gillis, Ann Arbor, MI (US)

(73) Assignee: Tri-State Hospital Supply Corp., Howell, MI (US)

( * ) Notice: Subject to any disclaimer, the term of this patent is extended or adjusted under 35 U.S.C. 154(b) by 103 days.

(21) Appl. No.: 10/112,804

(22) Filed: Mar. 29, 2002

(51) Int. Cl.⁷ .............................................. A61B 17/42
(52) U.S. Cl. ...................................... 606/120; 606/207
(58) Field of Search ..................... 606/119–122, 174, 606/205–210

(56) References Cited

U.S. PATENT DOCUMENTS

| | | | | |
|---|---|---|---|---|
| 4,026,294 A | * | 5/1977 | Mattler | 606/120 |
| 4,803,983 A | * | 2/1989 | Siegel | 606/174 |
| 5,009,657 A | * | 4/1991 | Cotey et al. | 606/120 |
| 5,624,454 A | * | 4/1997 | Palti et al. | 606/174 |

* cited by examiner

Primary Examiner—Kevin T. Truong
(74) Attorney, Agent, or Firm—Fildes & Outland, P.C.

(57) ABSTRACT

An umbilical cord clamp cutter includes first and second handle portions including a grasping end and a cutting end. The cutting end includes a notch having a beveled cutting edge disposed proximate the terminus of the cutting end. A connector pivotably connects the handle portions between the grasping and cutting ends whereby the notches oppose one another. Movement of the grasping ends toward one another causes the cutting end notches to slide past one another capturing an umbilical cord clamp allowing the umbilical cord clamp to be cut.

8 Claims, 3 Drawing Sheets

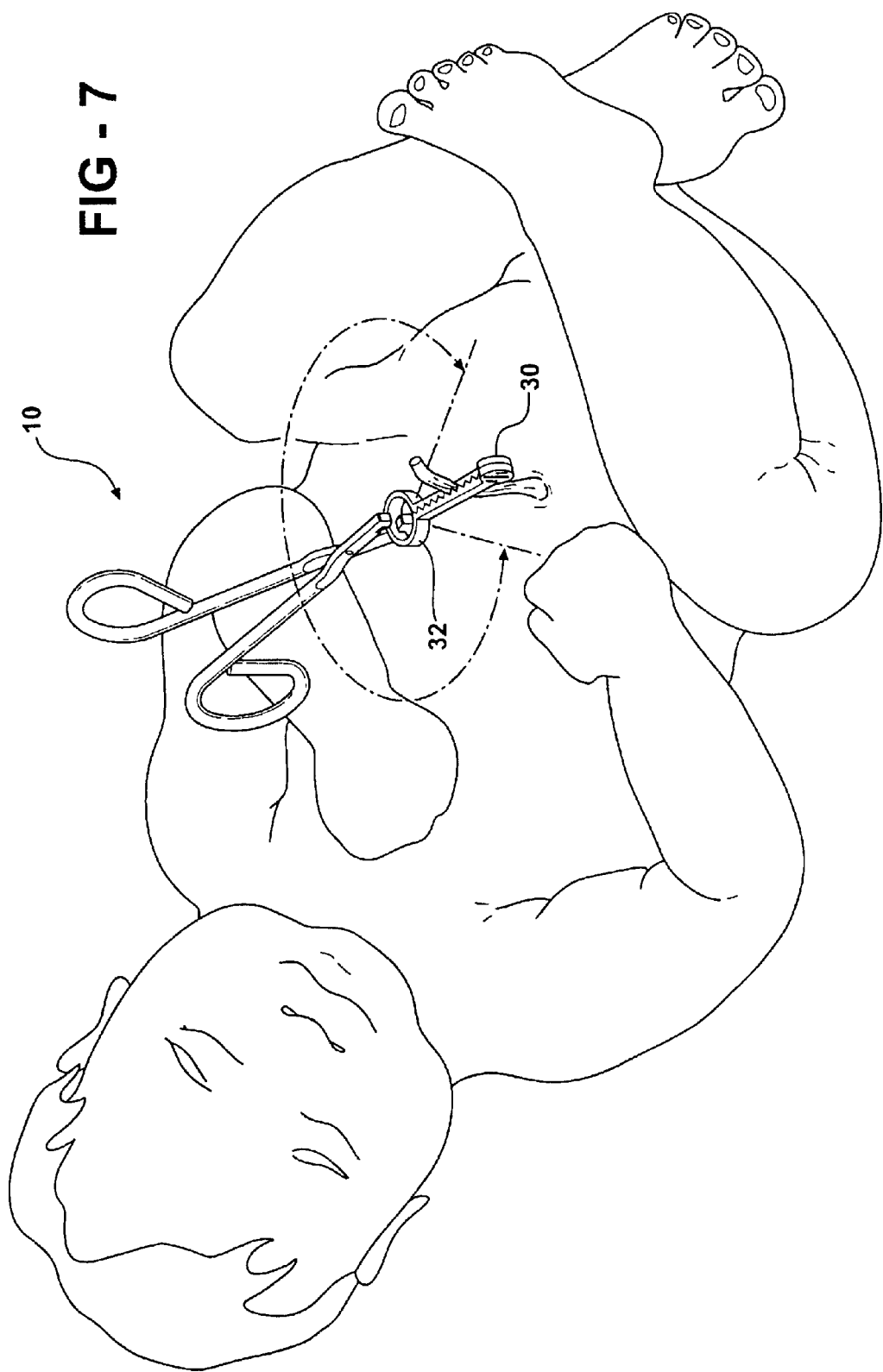

UMBILICAL CORD CLAMP CUTTER

TECHNICAL FIELD

This invention relates to medical instruments used for cutting and more particularly to an umbilical cord clamp cutter.

BACKGROUND OF THE INVENTION

Conventional umbilical cord clamp cutter instruments include a cutting blade formed at an end of one handle and a holder notch formed near an end of a second handle. The handles are pivotably connected together in scissors fashion. An umbilical cord clamp to be cut has the notch fitted over it, and the handles are urged toward one another to cut the clamp.

These clamp cutters are typically diecast, machined, riveted, peened and chrome plated. They are expensive and although re-useable, have to be manually cleaned and sterilized between uses. This process of pre-cleaning and disinfecting and/or sterilizing the cutting blades, or blade and anvil, can lead to the laceration of a cleaning technicians' fingers. To solve this clinical problem the inventors have devised an umbilical cord clamp cutter which is single patient use disposable, at a very low cost, but yet strong enough to cut through the thickest webs of plastic on all umbilical cord clamps on the market without the blades bending, camming, or spreading apart during the cut; or without the clamp and it's captured umbilical cord stump twisting or tugging relative to the clinician's chosen, held position of the cutter, as the web cutting action is made.

SUMMARY OF THE INVENTION

The present invention provides a low cost, single patient use, disposable umbilical cord clamp cutter that is strong enough to eliminate the camming action and blade spreading that is typically encountered if ordinary low cost cutters (such as scissors and the like) are engaged in an attempt to cut umbilical cord clamps off of infants.

The present invention also provides a wire instrument type of umbilical cord clamp cutter having improved cutting action that does not twist the clamp and the infant's umbilical stump, relative to the held position of the cutter.

An umbilical cord clamp cutter of the invention includes first and second handle portions. Each handle portion includes a grasping end and a cutting end. The cutting end includes a notch having a cutting edge disposed proximate the terminus of the cutting end. A connector pivotably connects the handle portions between the grasping and cutting ends whereby the notches oppose one another. Movement of the grasping ends toward one another causes the cutting end notches to slide past one another allowing an umbilical cord clamp to be cut, without the umbilical cord stump and clamp rotating, twisting or tugging relative to the held position of cutter.

In a preferred embodiment each notch includes a base and that base includes a bevel defining a cutting edge. The bevel is generally 45°, but can be more, or less. Further each notch is generally rectangular in shape and the tendency of the cord clamp to be moved relative to one end or the other during the cutting is eliminated.

A method of cutting an umbilical cord clamp includes the steps of:

positioning the web of an umbilical cord clamp to be cut between opposed notches in cutting ends of an umbilical cord clamp cutter including pivotably connected first and second handle portions having grasping ends extending from the cutting ends; and moving the grasping ends toward one another to cause the cutting end notches to slide past one another and cut the umbilical cord clamp.

The step of the cutter inherently holding and stabilizing the umbilical cord clamp in the notches of the cutter in such a way that when the cut through the web is made, the clamp and umbilical stump is not twisted and tugged relative to the clinician's held position of the cutter.

These and other features and advantages of the invention will be more fully understood from the following detailed description of the invention taken together with the accompanying drawings.

BRIEF DESCRIPTION OF THE DRAWINGS

In the drawings:

FIG. 7 is an environmental schematic view illustrating an infant with a clamped umbilical cord stump, an umbilical cord clamp cutter disposed in a plane generally normal to the plane of the web of a cord clamp, and relative possible positioning of the umbilical cord clamp cutter constructed in accordance with the invention.

DETAILED DESCRIPTION OF THE INVENTION

Figure 1:
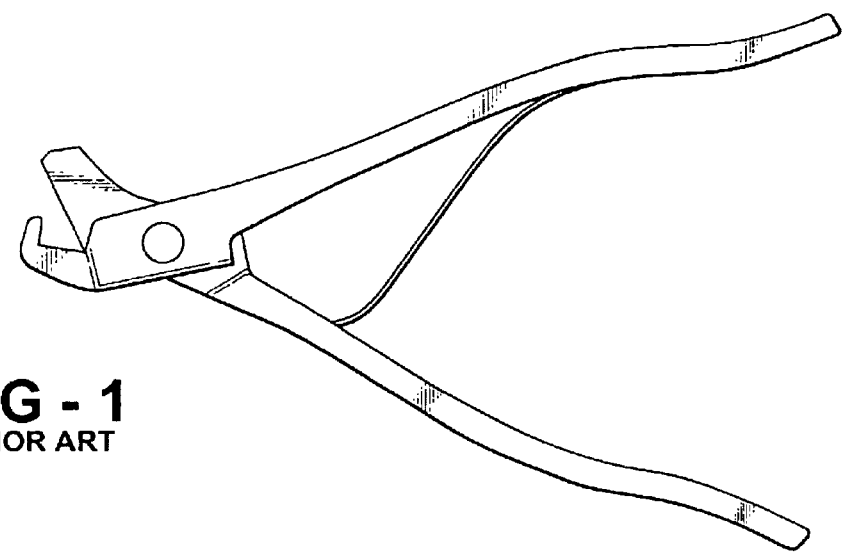
FIG. 1 is a plan view of a prior art umbilical cord clamp cutter.
Figure 2:
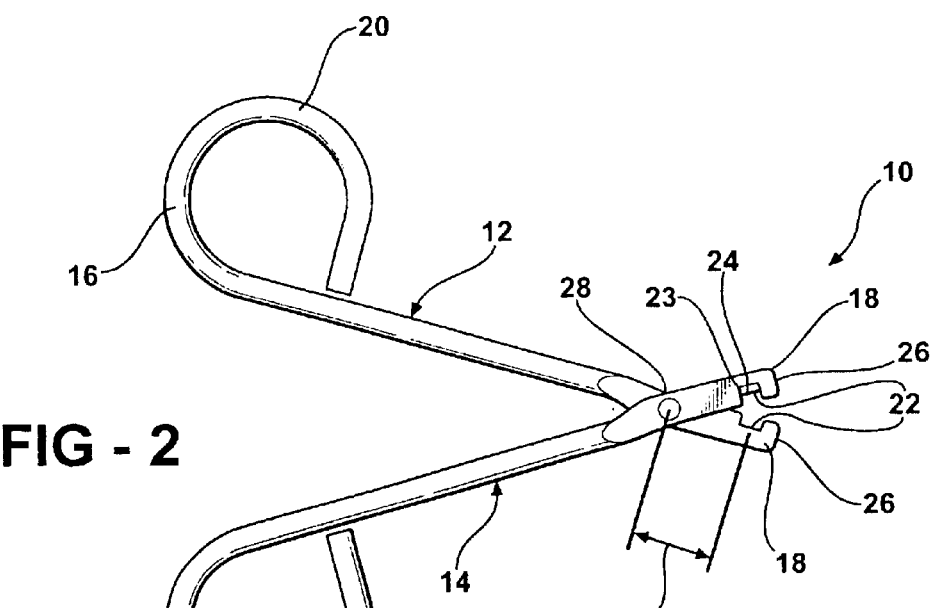
FIG. 2 is a plan view of an umbilical cord clamp cutter constructed in accordance with the invention illustrated in an open position.
Figure 3:
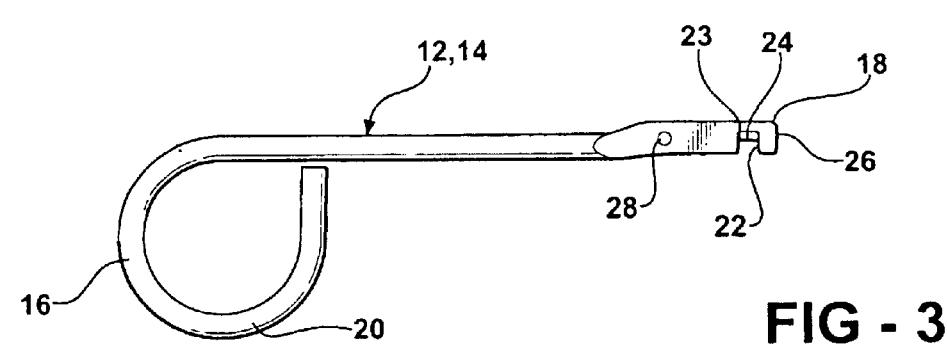
FIG. 3 is a plan view of a handle portion of the cutter of FIG. 2 illustrating a grasping and cutting end including a notch.
Figure 4:
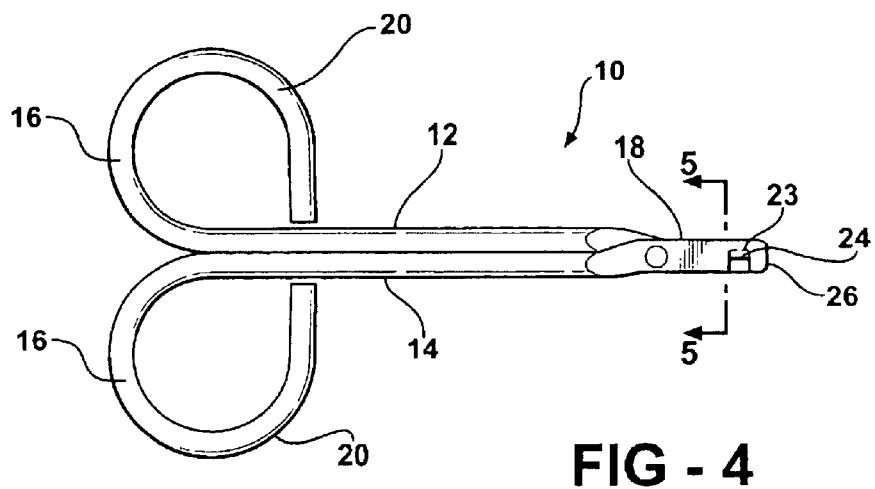
FIG. 4 is a plan view of the umbilical cord clamp cutter of FIG. 2 illustrated in a closed position where opposed beveled edges have slid past one another.

Referring now to the drawings in detail, numeral 10 generally indicates an umbilical cord clamp cutter used for cutting the plastic umbilical cord clamp off the umbilical cord at a later date, post birth. As is hereinafter more fully described, the clamp cutter eliminates the blade-relative-to-blade camming and separation action that is typically encountered if low cost cutters (such as scissors and the like) are engaged in attempts to provide a disposable cutter; and provides a low cost, single use, disposable cord clamp cutter.

Figure 5:
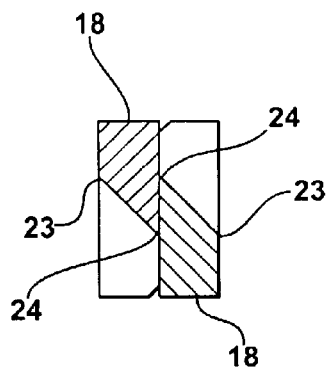
FIG. 5 is a sectional view taken along lines 5—5 in FIG. 4 illustrating the cooperation of beveled cutting edges of the notches.

As illustrated in FIGS. 2–5, clamp cutter 10 includes first and second handle portions 12, 14 made of a formed and stamped metal wire. Each handle portion 12, 14 includes a grasping end 16 and a cutting end 18. Handle end 16 includes a loop 20 formed therein to facilitate finger interface by a user. Cutting end 18 includes a notch 22 having a base 23 including a beveled cutting edge 24 as illustrated in FIG. 5.

Notch 22 may be of a generally rectangular shape adapted to fit the typical rectangular plastic web of the closure hinge on typical umbilical cord stump clamps in the marketplace. Notch 22 is disposed proximate the terminus 26 of the cutting end 18.

A connector 28, such as a rivet or other strong fastener, pivotably connects handle portions 12, 14 between the grasping and cutting ends 16, 18. As illustrated in the drawings, notches 22 of the handle portions 12, 14 oppose one another and upon sliding past one another as the handles are moved from the open position, FIG. 2, to the closed position, FIG. 4, can cut an umbilical cord clamp without the blades spreading from one another, due to the combination of the short distance, L, from notch 22 to connector 28, a fairly steep cutting angle of 45° or more, the strength of the chosen rivet, and the gauge of the stamped/formed metal wire. As can be seen with reference to FIG. 5, the cutting ends 18 are urged toward one another as the beveled edges 24 cut through a cord clamp.

In a preferred embodiment, beveled cutting edge 24 is generally 45° or greater. The metal wire of the handle portions 12, 14 is 8–10 gauge wire.

Figure 6:
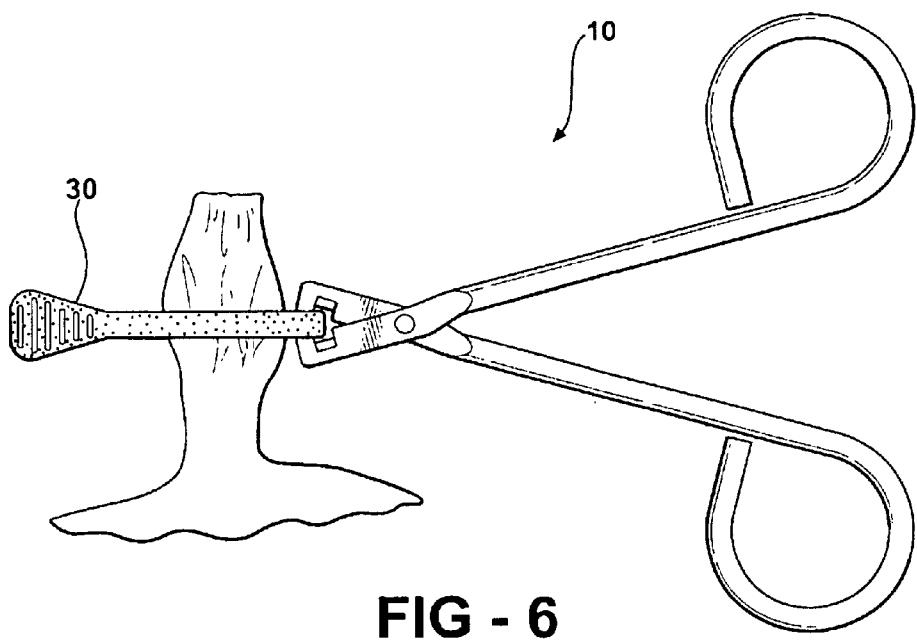
FIG. 6 is an environmental view illustrating a method of cutting an umbilical cord clamp wherein the clamp and umbilical cord stump are held stable against twisting, tugging or rotation relative to the held position of the cutter, during the cutting action.

A method of cutting an umbilical cord clamp with the invention 10 is illustrated in FIGS. 6 and 7 includes the steps of positioning opposed notches 22 in the cutting ends 18 of the cord clamp cutter around the web 32 of an umbilical cord clamp to be cut. The cutter 10 is positioned in a plane disposed generally perpendicular to the plane of the web. The clinician or nurse may place the cutter 10 at any position around the circumference of the web to facilitate easy and unfettered access to the infant from various positions/directions.

A cut through the clamp web 32 is made as the grasping ends 16 of the handle portions 12, 14 are urged toward one another and the cutting notches 22 slide past one another. Thereby the clamp 30 does not twist or rotate due to the confining nature of the notch, and wherein the clamp does not rotate about another axis relative to cutter due to high cutting angle of 45° or more. Furthermore, the cutting ends 18 do not spread apart and stop cutting due to short "L", a strong rivet, a 45° cutting angle, and adequate wire gauge as can occur with other low cost cutters, not designed for a clamp cutting application.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. An umbilical cord clamp cutter comprising:
   first and second handle portions;
   each said handle portion having a grasping end and a cutting end;
   each said cutting end including a notch therein having a cutting edge disposed proximate the terminus of the cutting end; and
   a connector pivotably connecting said handle portions between said grasping and cutting ends whereby said notches oppose one another and movement of said grasping ends toward one another causes the cutting end notches to slide past one another capturing the umbilical cord clamp and cutting the clamp.

2. The umbilical cord clamp cutter of claim 1 wherein each notch includes a base and said base includes a bevel defining a cutting edge.

3. The umbilical cord clamp cutter of claim 2 wherein said bevel is generally 45°.

4. The umbilical cord clamp cutter of claim 1 wherein each notch is generally rectangular in shape.

5. The umbilical cord clamp cutter of claim 1 wherein said handle portions are formed from stamped metal wire.

6. The umbilical cord clamp cutter of claim 5 wherein said metal wire is 8–10 gauge wire.

7. A method of cutting a plastic umbilical cord clamp comprising the steps of:
   positioning opposed notches of an umbilical cord clamp cutter around the web of an umbilical cord clamp to be cut, said clamp cutter including pivotably connected first and second handle portions having grasping ends extending from the cutting ends, and each said notch including a base having a beveled cutting edge;
   aligning the clamp cutter in a plane generally normal to the plane of the web; and
   moving the grasping ends toward one another to cause the cutting end notches to slide past one another capturing the umbilical cord clamp web and cutting the umbilical cord clamp without twisting and rotating the clamp.

8. The method of claim 7 including the step of stabilizing the umbilical cord clamp in said notches by holding the plastic clamp rigidly perpendicular to the plane of the cutting ends while making the cut through the clamp.

* * * * *